United States Patent
Chang et al.

(10) Patent No.: US 12,208,185 B2
(45) Date of Patent: Jan. 28, 2025

(54) BREAST PUMP HOUSING AND FLANGE ASSEMBLY

(71) Applicant: Willow Innovations, Inc., Mountain View, CA (US)

(72) Inventors: John Chang, Los Altos, CA (US); Brian Mason, Lexington, MA (US); Mathew Calmer, Sacramento, CA (US); Naomi Kelman, Los Altos Hills, CA (US); Julie Vrany Phillips, Los Altos, CA (US); Michelle Deng, Menlo Park, CA (US); David Jennings Dostal, Hanover, NH (US); Daniel Zisuk Lee, Queensbury, NY (US)

(73) Assignee: Willow Innovations, Inc., Mountain View, CA (US)

( * ) Notice: Subject to any disclaimer, the term of this patent is extended or adjusted under 35 U.S.C. 154(b) by 1000 days.

(21) Appl. No.: 17/182,398

(22) Filed: Feb. 23, 2021

(65) Prior Publication Data

US 2021/0196872 A1     Jul. 1, 2021

Related U.S. Application Data

(63) Continuation of application No. PCT/US2019/048069, filed on Aug. 26, 2019.

(60) Provisional application No. 62/788,780, filed on Jan. 5, 2019, provisional application No. 62/723,383, filed on Aug. 27, 2018.

(51) Int. Cl.
A61M 1/06     (2006.01)

(52) U.S. Cl.
CPC .............. *A61M 1/064* (2014.02); *A61M 1/06* (2013.01); *A61M 1/062* (2014.02); *A61M 1/067* (2021.05)

(58) Field of Classification Search
CPC ...... A61M 1/06; A61M 1/0697; A61M 1/064; A61M 1/062; A61M 1/06935; A61M 1/067; A61M 1/066; A61M 1/75
See application file for complete search history.

(56) References Cited

U.S. PATENT DOCUMENTS

| | | |
|---|---|---|
| 1,197,011 A | 9/1916 | Cilino |
| 4,263,912 A | 4/1981 | Adams |
| 4,311,141 A | 1/1982 | Diamond |
| 4,768,547 A | 9/1988 | Danby |
| 4,821,580 A | 4/1989 | Jomitsma |
| 5,542,921 A | 8/1996 | Meyers et al. |

(Continued)

FOREIGN PATENT DOCUMENTS

| | | |
|---|---|---|
| CN | 2628060 Y | 7/2004 |
| CN | 201692384 | 1/2011 |

(Continued)

OTHER PUBLICATIONS

Jobmaster Magnets Canada Inc. Aug. 9, 2015 <https://www.jobmastermagnets.com/magnetic-coatings-and-adhesives> (Year: 2015).*

(Continued)

*Primary Examiner* — Scott J Medway

(57) ABSTRACT

A housing and flange assembly arrangement for a breast pump system including or involving a flange having transparent and other structure for facilitating alignment of the breast pump on a breast, and includes structure facilitating ease of assembly of a housing for the breast pump.

15 Claims, 5 Drawing Sheets

(56) References Cited

U.S. PATENT DOCUMENTS

| | | |
|---|---|---|
| 5,634,468 A | 6/1997 | Platt et al. |
| 5,658,133 A | 8/1997 | Anderson et al. |
| 5,810,772 A | 9/1998 | Niederberger |
| 5,827,191 A | 10/1998 | Rosenfeld |
| 6,273,868 B1 | 8/2001 | Nordvik |
| 6,287,252 B1 | 9/2001 | Lugo |
| 6,328,082 B1 | 12/2001 | Lafond |
| D459,233 S | 6/2002 | Young |
| 6,440,100 B1 | 8/2002 | Prentiss |
| 6,547,756 B1 | 4/2003 | Greter et al. |
| 6,579,258 B1 | 6/2003 | Atkin et al. |
| 6,689,073 B2 * | 2/2004 | Quay .................. C12Q 1/6886 604/74 |
| 6,712,785 B2 | 3/2004 | Morton et al. |
| 6,840,918 B1 | 1/2005 | Britto et al. |
| 7,201,735 B2 | 4/2007 | Atkin et al. |
| 7,223,255 B2 | 5/2007 | Myers et al. |
| 7,621,797 B1 | 11/2009 | Hershkovich |
| 7,824,363 B2 | 11/2010 | Myers |
| 7,972,297 B2 | 7/2011 | Bryan et al. |
| 7,988,661 B2 | 8/2011 | Silver et al. |
| 8,057,425 B1 | 11/2011 | Myers et al. |
| 8,070,715 B2 | 12/2011 | Quackenbush et al. |
| 8,070,716 B2 | 12/2011 | Sutrina et al. |
| 8,262,606 B2 | 9/2012 | Greter et al. |
| 8,282,596 B2 | 10/2012 | Greter et al. |
| 8,353,865 B2 | 1/2013 | Thilwind et al. |
| 8,357,116 B2 | 1/2013 | Simdon |
| 8,376,986 B2 | 2/2013 | Van Schijndel et al. |
| 8,671,701 B2 | 3/2014 | McKendry |
| 8,684,961 B2 | 4/2014 | Gottenbos et al. |
| 8,801,495 B1 | 8/2014 | Guindon |
| 9,050,404 B2 | 6/2015 | Silver et al. |
| 9,162,016 B2 | 10/2015 | Geddes |
| 9,173,587 B2 | 11/2015 | Van Schijndel et al. |
| 9,199,017 B2 | 12/2015 | Greter |
| 9,278,167 B2 | 3/2016 | Aalders et al. |
| 10,105,474 B2 | 10/2018 | Barral et al. |
| 10,434,228 B2 * | 10/2019 | Chang .................. A61M 1/067 |
| 10,625,005 B2 | 4/2020 | Chang et al. |
| 10,675,005 B2 | 4/2020 | Chang et al. |
| 10,881,766 B2 | 1/2021 | O'Toole et al. |
| 2003/0191433 A1 | 10/2003 | Prentiss |
| 2004/0024351 A1 | 2/2004 | Greter et al. |
| 2004/0101414 A1 | 5/2004 | Gharib et al. |
| 2004/0127845 A1 | 7/2004 | Renz et al. |
| 2005/0059928 A1 | 3/2005 | Larsson |
| 2005/0131332 A1 | 6/2005 | Kelly et al. |
| 2005/0234370 A1 | 10/2005 | Beal et al. |
| 2006/0106334 A1 | 5/2006 | Jordan et al. |
| 2007/0219486 A1 * | 9/2007 | Myers .................. A61M 1/067 604/74 |
| 2008/0045888 A1 | 2/2008 | Edwards et al. |
| 2008/0177224 A1 | 7/2008 | Kelly et al. |
| 2008/0243059 A1 | 10/2008 | Yamashita et al. |
| 2009/0024080 A1 | 1/2009 | Rohrig |
| 2010/0010682 A1 | 4/2010 | Zhou |
| 2010/0106082 A1 | 4/2010 | Zhou |
| 2010/0217148 A1 | 8/2010 | Binder |
| 2011/0071466 A1 | 3/2011 | Silver et al. |
| 2011/0196291 A1 | 8/2011 | Vischer et al. |
| 2011/0245763 A1 | 10/2011 | Myers |
| 2011/0270162 A1 | 11/2011 | Guo |
| 2012/0004603 A1 * | 1/2012 | Harari .................. A61B 5/6831 604/74 |
| 2012/0101575 A1 | 4/2012 | Horne et al. |
| 2012/0277636 A1 | 11/2012 | Blondheim et al. |
| 2012/0277728 A1 | 11/2012 | Weber et al. |
| 2013/0023821 A1 | 1/2013 | Khalil et al. |
| 2013/0123688 A1 | 5/2013 | Bosman et al. |
| 2013/0131588 A1 | 5/2013 | Silver et al. |
| 2013/0177455 A1 | 7/2013 | Kamen et al. |
| 2013/0294882 A1 | 11/2013 | Christy et al. |
| 2014/0066734 A1 | 3/2014 | Zdeblick |
| 2014/0288466 A1 * | 9/2014 | Alvarez .................. A61M 1/062 601/84 |
| 2014/0378895 A1 | 12/2014 | Barack |
| 2014/0378946 A1 | 12/2014 | Thompson et al. |
| 2015/0065994 A1 | 3/2015 | Fridman et al. |
| 2015/0100016 A1 | 4/2015 | Liao |
| 2015/0148709 A1 | 5/2015 | Mardiks et al. |
| 2015/0196247 A1 | 7/2015 | Lau |
| 2015/0292500 A1 | 10/2015 | Girard et al. |
| 2016/0015876 A1 | 1/2016 | Tattersfield et al. |
| 2016/0082165 A1 | 3/2016 | Alvarez et al. |
| 2016/0206794 A1 * | 7/2016 | Makower .................. A61M 1/06 |
| 2016/0256618 A1 | 9/2016 | Embleton |
| 2016/0287769 A1 | 10/2016 | Makower et al. |
| 2017/0072118 A1 | 3/2017 | Makower et al. |
| 2017/0080134 A1 | 3/2017 | Makower et al. |
| 2017/0173232 A1 | 6/2017 | Chang et al. |
| 2018/0339089 A1 | 11/2018 | Chang et al. |

FOREIGN PATENT DOCUMENTS

| | | |
|---|---|---|
| EP | 2456482 B1 | 11/2016 |
| EP | 3151876 B1 | 11/2017 |
| GB | 2342446 A | 4/2000 |
| JP | 2005279044 | 10/2005 |
| RU | 2012 107356 | 5/2012 |
| WO | WO1996022116 | 7/1996 |
| WO | WO 2000/57934 | 10/2000 |
| WO | WO2001054488 | 8/2001 |
| WO | WO2011010255 | 1/2011 |
| WO | WO2011144984 A | 11/2011 |
| WO | WO2012037848 | 3/2012 |
| WO | WO2012037848 A1 | 3/2012 |
| WO | WO 2013076055 | 5/2013 |
| WO | WO2013088310 | 6/2013 |
| WO | WO 2013/187763 | 12/2013 |
| WO | WO2013184004 | 12/2013 |
| WO | WO2015120321 | 8/2015 |

OTHER PUBLICATIONS

Chiu et al., Development of a piezoelectric polyvinylidene fluoride (PVDF) polymer-based sensor patch for simultaneous heartbeat and respiration monitoring, Sensors and Actuators A: Physical, vol. 189, Jan. 2013, pp. 328-334.

Double Electric Breast Pump/Dr. Brown's, http://www.drbrownsbaby.com/breastfeeding-product/breast-pumps/double-electric, May 15, 2014.

* cited by examiner

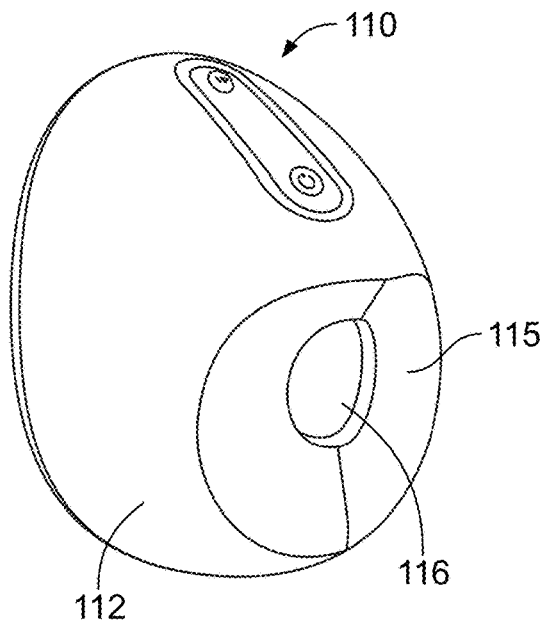
FIG. 11
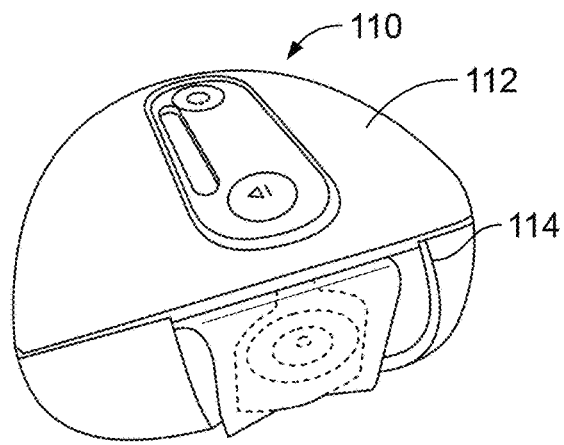
FIG. 12
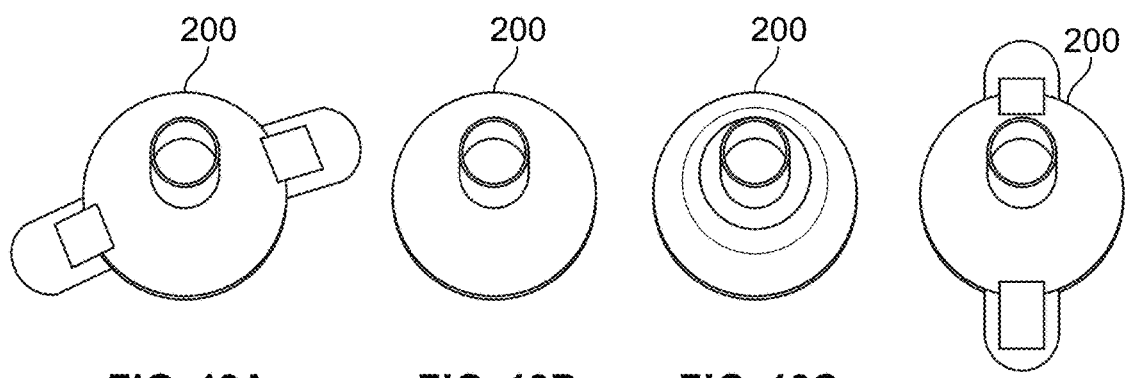
FIG. 13A　　FIG. 13B　　FIG. 13C　　FIG. 13D

BREAST PUMP HOUSING AND FLANGE ASSEMBLY

BACKGROUND OF THE DISCLOSURE

The present disclosure relates to breast pumps generally, and in particular to housing and flange assemblies for breast pumps.

As more women become aware that breastfeeding is the best source of nutrition for a baby, and also offers health benefits to the nursing mother, the need is increasing for breast pump solutions that are user-friendly, quiet, discrete and versatile for use by a nursing mother in various situations. This is particularly true for the working mother, who is away from the home for eight to ten hours or more and needs to pump breast milk in order to have it available for her baby, but it is also a requirement for many other situations where the mother is away from the privacy of the home for an extended period, such as during shopping, going out to dinner or other activities.

Although a variety of breast pumps are available, a number are awkward and cumbersome, requiring many parts and assemblies and being difficult to transport. Hand pump varieties that are manually driven are onerous to use and can be inconvenient to use. Some powered breast pumps require an AC power source to plug into during use. Some systems are battery driven, but draw down the battery power fairly rapidly as the motorized pump continuously operates to maintain suction during the milk extraction process. Certain other of the breast pumps available are lacking in structure that facilitates proper or desired alignment of the breast pump with the user's breast. Moreover, certain breast pumps lack structure that is easy to assemble. There is thus a continuing need for conveniently usable and effective approach to attachable and replaceable assemblies for a portable wearable breast pump.

The present disclosure addresses these and other needs.

SUMMARY OF THE DISCLOSURE

Briefly and in general terms, the present disclosure is directed towards housing and flange assemblies for a breast pump system. In a preferred embodiment, the flange includes transparent and other structure for facilitating alignment of the breast pump on a breast. The preferred embodiment additionally includes structure facilitating ease of assembly of a housing for the breast pump.

In one aspect, the breast pump system includes structure that improves an ability to see anatomy while aligning a breast pump flange with breast anatomy. In one approach, the flange is formed from relatively clear or transparent grades of polypropylene or other similar materials. The flange is alternatively or additionally configured with a generally flat window to allow visualization and/or confirmation of alignment with breast anatomy.

In another aspect, the breast pump system is equipped with convenient and easy to use structure configured to connect housing structure. In one approach, magnets are configured on breast pump housing structure. Magnet to magnet or magnet to metal elements are employed as connecting structure between the flange and a shell or pump housing, the same facilitating ease of holding the flange to a breast and then attaching the pump to the flange without needing to move or shift the flange on the breast. Such an approach to connection provides tactile and/or audible confirmation of attachment between breast pump components. In alternative approaches to attachment between breast pump assembly components, there can be provided a combination of hooks or other elements and magnets.

These and other features of the disclosure will become apparent to those persons skilled in the art upon reading the details of the systems and methods as more fully described below.

BRIEF DESCRIPTION OF THE DRAWINGS

FIG. 11 is a perspective view, depicting a cut-out feature incorporated into a shell.

FIG. 12 is a top view, depicting structure facilitating flow visibility.

FIGS. 13A-D are front views, depicting various approaches to auxillary flanges.

DETAILED DESCRIPTION OF THE DISCLOSURE

Before the present systems and methods are described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, the preferred methods and materials are now described.

It must be noted that as used herein and in the appended claims, the singular forms "a", "an", and "the" include plural referents unless the context clearly dictates otherwise. Thus, for example, reference to "a sensor" includes a plurality of such sensors and reference to "the system" includes reference to one or more systems and equivalents thereof known to those skilled in the art, and so forth.

Various details of the breast pump system can be found in U.S. patent Ser. No. 16/050,201 filed Jul. 31, 2018, the contents of which is hereby incorporated herein by reference thereto.

Figure 1:
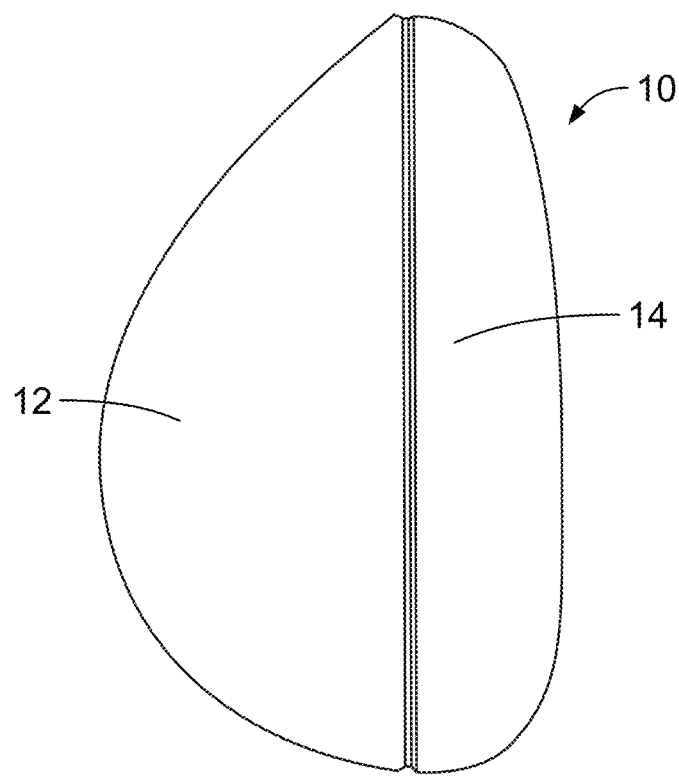
FIG. 1 is a side view, depicting a breast pump system.

With reference to FIG. 1, there is shown a breast pump system 10 according to an embodiment of the present disclosure. The breast pump system 10 can include one or more of the below introduced or described features or functions, or a combination thereof. The housing or outer shell 12 of system 10 can be shaped and configured to be contoured to the breast of a user and to thus provide a more natural appearance when under the clothing of the user. As can be appreciated from the figures, the system can define a natural breast profile. The natural breast profile is contemplated to fit comfortably and conveniently into a bra of a user and to present a natural look. As such, the profile is characterized by having a non-circular base unlike that embodied in a generally dome-shaped configuration. Extending from the base are curved surfaces having asymmetric patterns. Moreover, like natural breasts, the profile of the device or system is contemplated to define one or more asymmetric curves and off-center inertial centers. Various natural breast shapes can be provided to choose from the tastes and needs of a user. An opposite side of the pump system 10 is configured with a flange 14 which is sized and shaped to engage a breast of a user. The flange 14 is contoured to comfortably fit against a wide range of user's bodies and to provide structure for sealingly engaging with breast tissue. In one particular embodiment, the flange 14 can form generally rigid structure, and alternatively or additionally unlike a standard flange can lack sharp edges or a lip portion against which breast tissue might be engaged during use. In this regard, the flange includes surfaces that extend outwardly from a nipple receiving portion of the flange to engage breast tissue, thus providing extra surface area for comfortably contacting tissue. Moreover, a flange ridge 15 that runs about an entire perimeter of the flange 14 provides structure for the user to grip when pulling the assembly from the breast.

Figure 2:
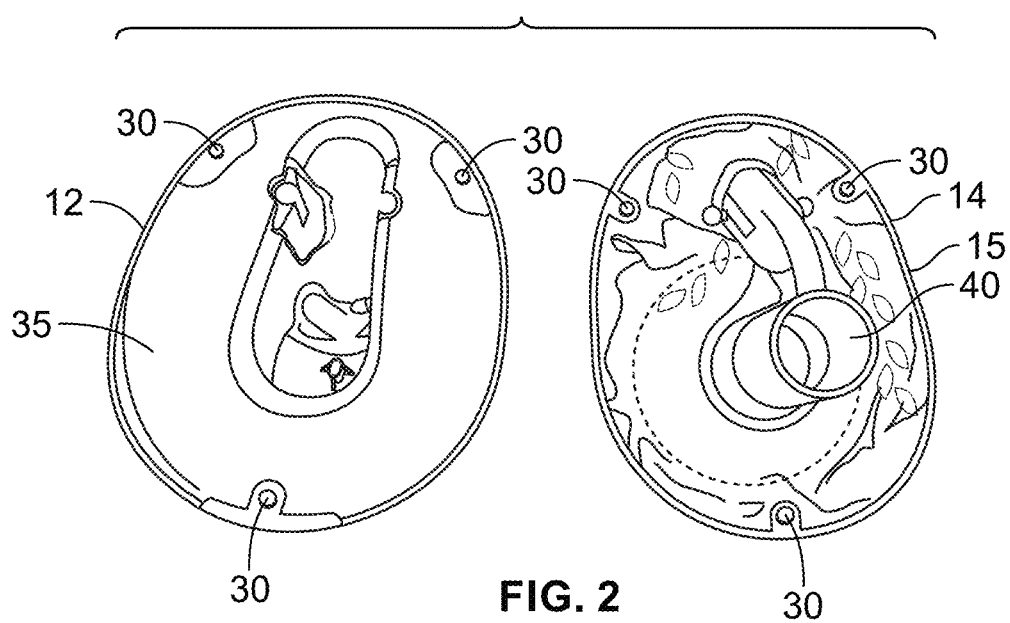
FIG. 2 are internal views, depicting the breast pump system of FIG. 1 in an unassembled state.

Referring now to FIG. 2, there is shown a breast pump system 10 with the flange 14 removed from the outer shell 12. Although various number and locations can be employed, as shown, there are provided a plurality of magnets 30 configured about both the perimeter of each of a chassis 35 and shell 12 breast pump assembly portion and the flange 14 portion. The magnets 30 are aligned to provide the system 10 with connecting structure between the flange and a shell housing, the same facilitating ease of holding the flange 14 to a breast and then attaching the pump 12, 35 to the flange 14 without needing to move or shift the flange on the breast. The magnet arrangement provides tactile and/or audible confirmation of attachment between breast pump components. The magnets can be hidden, exposed or coated, or a combination thereof. As stated, in alternative approaches to attachment between breast pump assembly components, there can be provided a combination of hooks or other elements and magnets.

In particular, in one or more approaches, the magnets 30 or other connecting structure or elements can be hidden under the chassis 35. For example, the bottom of the chassis 35 can include a flat hidden magnet. In one preferred embodiment, an exposed metal element is provided on the flange 14, an alternative to which is the utilization of covered or coated metal or magnets on the flange. In an alternative embodiment, such connecting structure and/or the flange can be covered to provide a cleaner appearance and also reduce corrosion such as by double coating with a thin polymer. The metal or magnets can be one or more of pill shaped, include rounded outer edges or assume bent rectangular shapes, or custom shapes and can be positioned on the flange 14, chassis 35 or shell 12 or perimeters thereof. Additionally, the flange 14 or portions thereof can alternatively or additionally be formed from stamped or MIM steel and in such an approach, the metal/magnet on the chassis/pump 35 side of the assembly can assume a custom shape matching or being larger than the surface area contact between connecting parts to ensure a solid attachment.

Further, the arrangement of materials is configured such that there will be no rust under normal breast pump system operating conditions. The sum magnet force shall be approximately 2.5 lb so that the breast pumps system 10 allows for variation in assembly techniques with the fluid container. The magnet forces may be distributed evenly across the plurality of magnets. The forces may also be distributed unevenly across the plurality of magnets to allow for preferred separation of the pump and flange—for example it may be preferred that the bottom portion of the flange separates sooner than the top portion of the flange from the pump assembly. The magnet approach to connection also provides protection against fluid ingress and survives dropping. Additionally, structure can be provided such that additional magnets can be added by the user.

Figure 3:
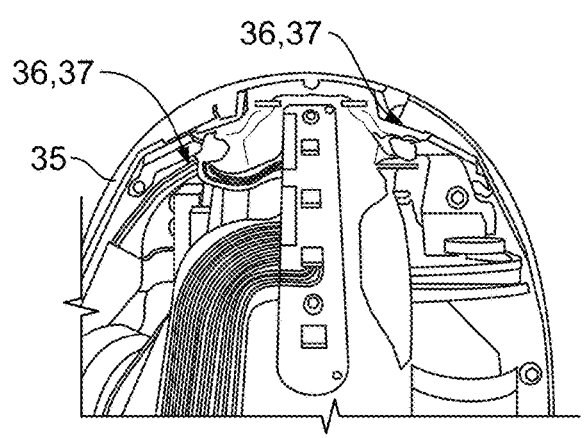
FIG. 3 is an internal view, depicting an alternative arrangement for attachment structure.
Figure 4:
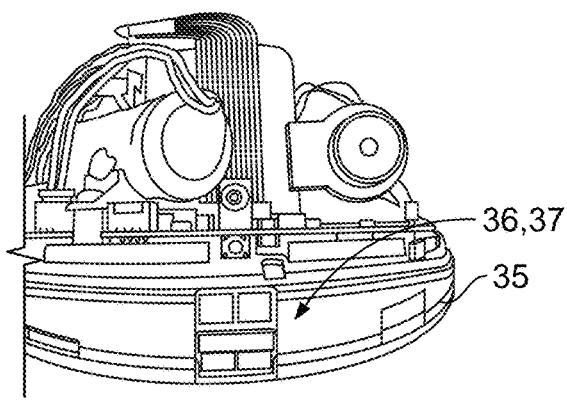
FIG. 4 is a bottom view, depicting an alternative arrangement for attachment structure.
Figure 5:
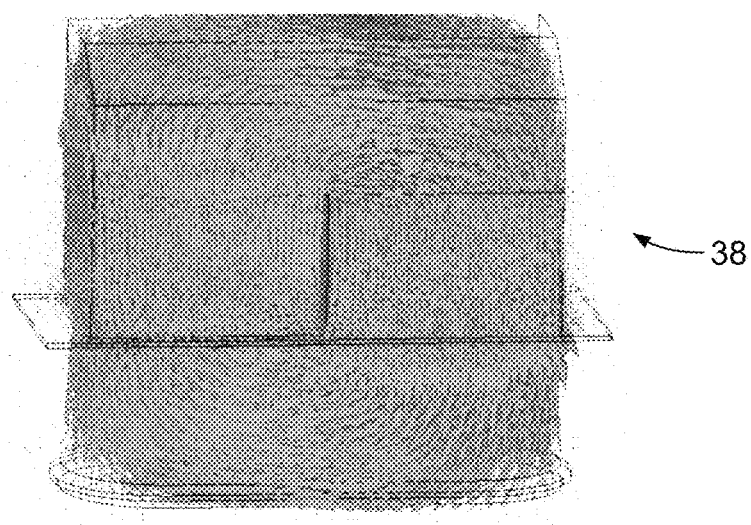
FIG. 5 is field representation, depicting magnetic fields created by a two magnet attachment approach.

In one particular approach, as shown in FIGS. 3 and 4, attachment structure is embodied in a shunt 36 and dual magnet 37 assembly. This approach is employed at various positions about a periphery of and under the chassis 35. With reference to FIG. 5, the two magnet approach provides a relatively tighter magnetic field 38 and results in a smaller space requirement that creates necessary and desired magnetic strength. The tighter magnetic field also results in not impacting other sensors such as a hall effect sensor. The shunt 36 is made from steel and functions to direct the magnetic field downwardly. The assembly provides a tight, quickly tapering magnetic field than a single magnet of the same combined size.

Figure 6:
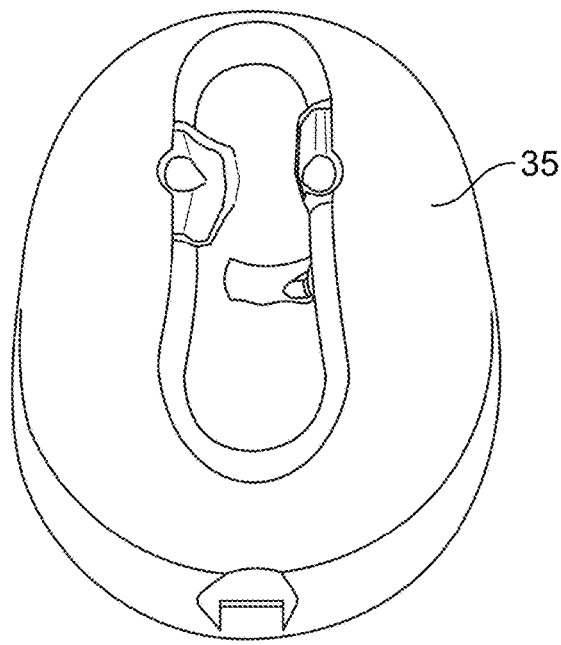
FIG. 6 is an external view, depicting a surface of the pump that receives a flange assembly.
Figure 7:
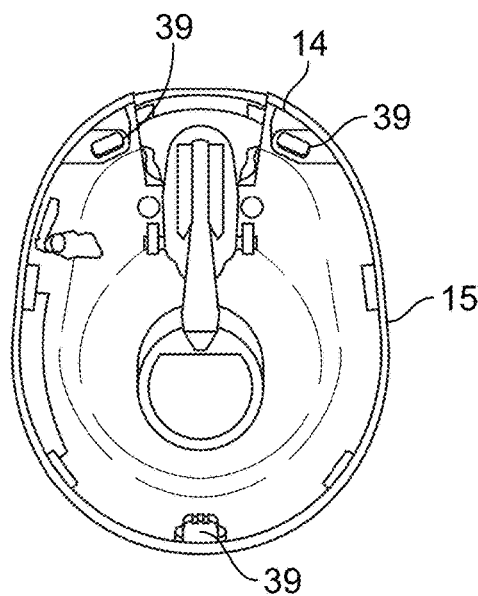
FIG. 7 is an internal view, depicting an internal surface of the flange.

With reference to FIG. 6, this shunt/magnet attachment arrangement allows for hiding the attachment structure under the chassis 35 to thereby provide a clean and smooth appearance presented to the flange 14, one that is not susceptible to corrosion or receptacles for milk to collect. The flange 14 (FIG. 7) is provided with stainless steel reaction plates 39 that align with the dual magnet/shunt assembly 36/37. In one approach, the reaction plates 39 are exposed in order to provide desired magnetic attachment strength. The reaction plates can be formed from ferromagnetic SST and is insert molded to ensure proper positioning and fit, and to avoid surfaces permitting debris collection. Additional structure 41 is also provided for facilitating the tucking of a collection container (not shown) within the flange 14.

Figure 8:
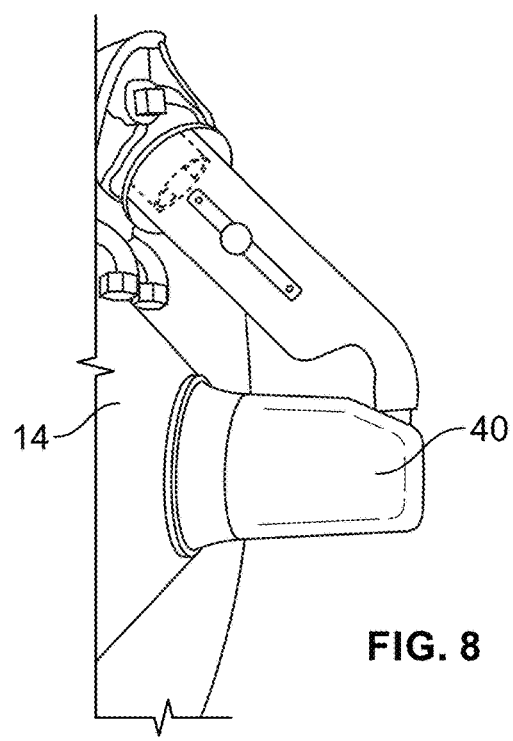
FIG. 8 is a side view, depicting the flange of the breast pump system.

As best seen in FIG. 8, the flange 14 includes structure that improves an ability to see anatomy while aligning a breast pump flange with breast anatomy, such as most effectively positioning a nipple within the flange 14. In one approach, the flange 14 is formed from relatively clear or transparent grades of polypropylene or other similar materials. The entirety or portions of the flange 14 can be formed from such material. The flange 14 is alternatively or additionally configured with a nipple receiving portion terminating with a generally flat 40 window to allow visualization and/or confirmation of alignment with breast anatomy. For example, the user can place the flange 14 on her breast and check positioning both through direct visualization through a transparent portion of the flange 14 as well as checking positioning by observing the breast and nipple through the window 40 and flange 14 reflection in a mirror.

Figure 9:
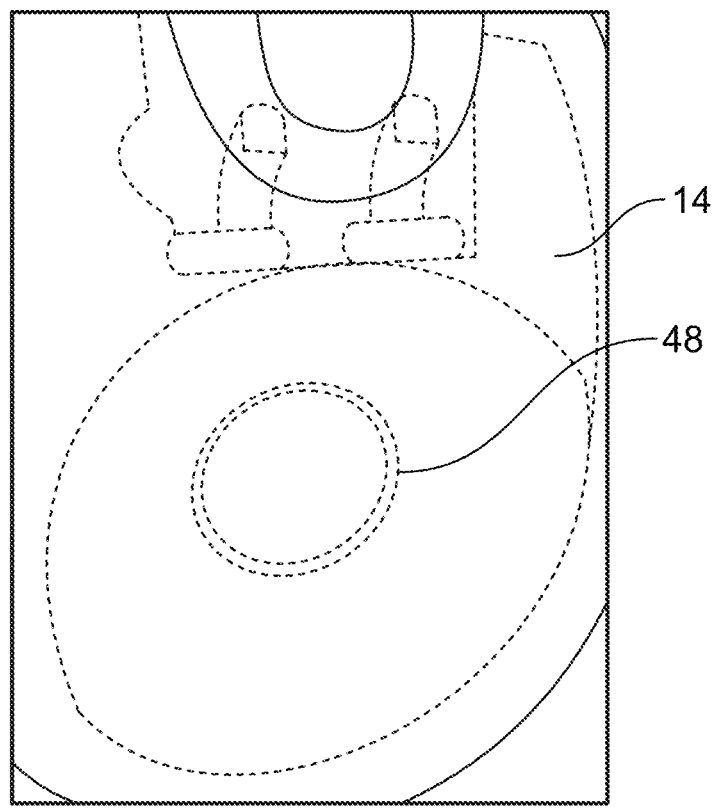
FIG. 9 is a partial front view, depicting a flange ring of a flange.

Thus, various approaches are contemplated for the flange 14 with respect to a user's nipple. One approach involves aligning the nipple within the flange 14 structure from the perspective of the mother from above. This perspective allows the user to view the nipple through the transparent flange 14 structure. The flat structure is characterized by producing less distortion than a curved surface. The user can also use a mirror or other reflective surface to view desired alignment though the window 40. Moreover, as shown in FIG. 9, the flange 14 is further provided with a flange ring 48 that facilitates confirming nipple alignment. In one aspect, the flange ring 48 is an in-molded feature that creates contrast via light reflection to assist the user to guide their nipple into the nipple receiving portion. Other structure can also be employed for this purpose as well such as a rubber band, or markings accomplishing this functionality can be provided by a sharpie for example. The location of these features can also cover various ranges for optimization of functionality.

Figure 10:
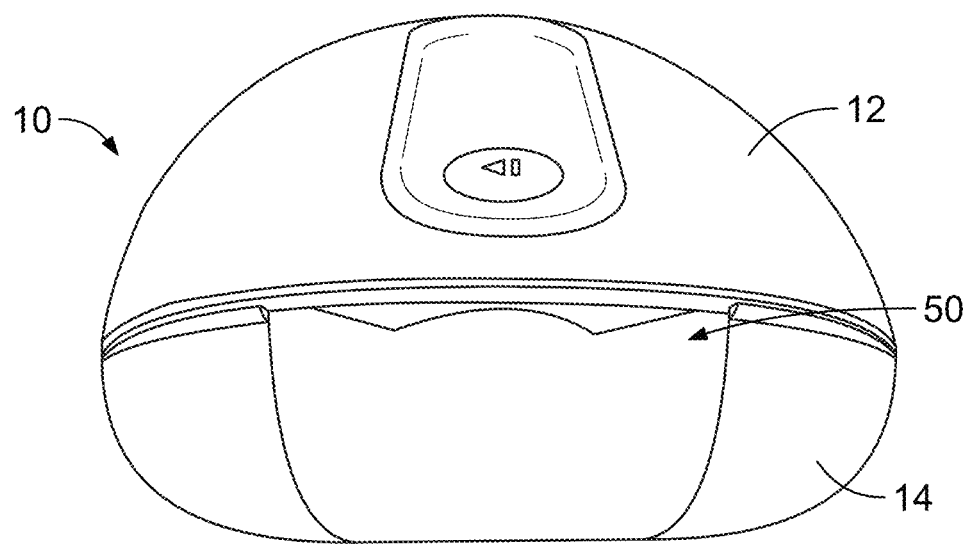
FIG. 10 is a top view, depicting scalloped structure incorporated into a pump assembly.

Turning to FIG. 10, there is shown a scalloped feature 50 formed into the flange 14 or a door assembly 52 attached thereto. The scalloped feature 50 provides a viewing path so that the user can see milk flowing from the breast and into the pump assembly.

Once the user determines that the flange 14 is properly positioned on the breast, the magnet-based attachment structure provides an efficient, effective and convenient approach to attaching the pump chassis 35 to the flange 14 while holding the flange 14 in place against the breast. A tactile or audible attachment between breast pump components provides confirmation that the breast pump system 10 is properly assembled. In an alternative or additional aspect, to check alignment the user can pause the pump (maybe by holding down a pause button) to bring the motor or system to a neutral state wherever system components are positioned so that the breast is still latched, but the system is not pumping, and the user could then pull off the breast pump, check nipple alignment, and then place the breast pump back on. All the while the flange is latched to the breast so there is no need to break latch, reintroduce air, or have to deal with milk in the flange Further structure and features are provided in yet other approaches to the pump assembly. With reference to FIGS. 11 and 12, there is shown a breast pump system 110 that includes an outer shell 112 including a cut-out feature 115 that provides a visual path to an interior of the breast pump, and in particular, visualization of the nipple receiving portion 116 of the flange 14. In this way, a user can ensure that nipple alignment is achieved or maintained when the pump is in its fully assembled and pumping configuration. To complete a breast shaped profile, a cap (not shown) is provided to mate with the outer shell 112 and cover the cut-out. In one embodiment, a mirror is provided within an interior of the cap so that a user can look into the nipple receiving portion and see their nipple. Alternatively, the cut-out is covered with a permanent clear cover so that the user can see into the breast pump, the permanent, fixed cover providing the system with the desired shape.

As best seen in FIG. 12, the door assembly attached to the flange 114 is removed or alternatively, made transparent (not shown) to provide further visualization of milk being pumped. Further, this structural approach allows the breast pump system 110 to be assembled on the breast. The flange 114 would be placed first, and then the pump chassis is attached to the flange 114 using the magnet attachment. Here, a flange ring can include a contrasting color so that it helps guidance upon the breast, or alternatively or additionally, can be magnetic to aid in attachment or be formed from a range of materials. Moreover, the peripheries of the flange can include extensions or additional material for holding by the user during assembling to the chassis 135.

Turning now to FIGS. 13A-D, there are shown various approaches to auxillary flanges 200 that a user places on their breast first to accomplish proper alignment. The remainder of a complete breast pump system (with its own flange) is then placed upon the auxillary flange 200, such as fitting the auxillary flange 200 within the breast pump system flange. The separate auxillary flange 200 can be formed from softer material than the breast pump system and define a low profile for mating with the breast pump system. This approach facilitates an effective and efficient approach to properly positioning the breast pump system for operation. The flanges 200 can also be adapted, customized or sized and shaped to fit certain breast sizes and shapes, allowing for the breast pump system to best mate with a particular user.

Accordingly, various approaches to attachment of breast system apparatus or assemblies are presented as well as alignment aid structure. The disclosed embodiments are configured to provide a convenient and effective approach to assembling components of a breast pump system, to improve on body alignment and milk flow, to visualize milk flow and assembly, and to facilitate ease of use.

While the present disclosure has been described with reference to the specific embodiments thereof, it should be understood by those skilled in the art that various changes may be made, and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the present disclosure.

That which is claimed is:

1. A breast pump system, comprising:
   a shell housing;
   a chassis received in the shell housing;
   a flange assembly including a nipple receiving portion, the nipple receiving portion including a terminal end configured with a flat window configured to allow visualization and confirmation of alignment of the flange assembly on a breast;
   a plurality of magnets attached to one or more of the shell housing, the chassis and the flange, the plurality of magnets configured to provide attaching structure between the shell housing and chassis and the flange assembly; and
   a sensor and a plurality of shunts, wherein the plurality of shunts are arranged to direct a magnetic field created by the plurality of magnets away from the sensor.

2. The system of claim 1, wherein one or more of the plurality of magnets are exposed.

3. The system of claim 1, wherein one or more of the plurality of magnets are hidden.

4. The system of claim 1, wherein one or more of the plurality of magnets are coated.

5. The system of claim 1, wherein the plurality of magnets or metal is positioned on both flange assembly and chassis and shell housing portions.

6. The system of claim 1, wherein the flange assembly is formed from transparent material.

7. The system of claim 1, wherein the flange assembly includes a magnet and the chassis includes a metal element or wherein the chassis includes a magnet and the flange includes a metal element.

8. The system of claim 1, wherein the connection between the flange assembly, chassis and shell housing is sufficient to hold the flange assembly, chassis and shell housing together as the breast pump system is filled with milk.

9. The system of claim 1, wherein the plurality of magnets provides a tactile or audible confirmation of attachment of the shell housing to the chassis and the flange assembly.

10. The system of claim 1, wherein one or more of the chassis, shell housing and flange assembly are configured to accept additional magnets.

11. The system of claim 1, further comprising a flange ring surrounding the nipple receiving portion of the flange assembly.

12. The system of claim 1, wherein the shell housing includes a cut-out that provides visualization of the flange assembly and milk flow.

13. The system of claim 1, wherein the flange assembly includes a scalloped portion arranged so that a user can visualize milk flow.

14. The system of claim 1, further comprising a plurality of reaction plates attached to the flange assembly, the reaction plates being aligned with the magnets.

15. The system of claim 1, the flange assembly further including an in-molded flange ring configured to facilitate confirming nipple alignment, the flange ring creating a contrast via light reflection to assist guiding a nipple into the nipple receiving portion.

* * * * *